United States Patent [19]

Schroeder et al.

[11] Patent Number: 5,281,417
[45] Date of Patent: Jan. 25, 1994

[54] ANTITUMOR PROCESS EMPLOYING NOVEL FERMENTATE OF AN ACTINOMADURA STRAIN

[75] Inventors: Daniel R. Schroeder, Higganum; Kin S. Lam, North Haven; Jacqueline M. Veitch, East Haven, all of Conn.

[73] Assignee: Bristol-Myers Squibb Company, New York, N.Y.

[21] Appl. No.: 17,223

[22] Filed: Feb. 12, 1993

Related U.S. Application Data

[62] Division of Ser. No. 780,516, Oct. 22, 1991.

[51] Int. Cl.$^5$ ............... C12P 1/06; C12R 1/03; A61K 35/00
[52] U.S. Cl. .................. 424/121; 435/171; 435/169; 435/252.1; 435/825
[58] Field of Search ............... 424/121; 435/71.1, 169, 435/252.1, 825

[56] References Cited

U.S. PATENT DOCUMENTS

| | | | |
|---|---|---|---|
| 3,859,598 | 8/1989 | Carter et al. | 435/252 |
| 4,420,473 | 12/1983 | Umezawa et al. | 435/169 |
| 4,551,533 | 11/1985 | Lee et al. | 546/35 |
| 4,578,468 | 3/1986 | Carter et al. | 546/35 |
| 4,615,975 | 10/1986 | Tunac | 435/825 |
| 4,774,184 | 9/1988 | Lee et al. | 435/118 |
| 4,845,037 | 7/1989 | Lee et al. | 435/252.1 |
| 4,921,700 | 5/1990 | Golick | 435/169 |
| 4,994,271 | 2/1991 | Lam et al. | 435/169 |
| 5,087,567 | 2/1992 | Dabrah et al. | 435/825 |

OTHER PUBLICATIONS

Napier et al, "Neocarzinostatin Chromophore", *Biochem. Biophys. Res. Commun.*, 89, (1979), pp. 635–642.
Suzuki et al., "Auromomycin Chromophore", *Biochem. Biophys. Res. Commun.*, 94, (1980), pp. 255–261.
Otani et al, "Isolation and Characterization of Non-protein Chromophore and its Degradation Product from Antibiotic C-1027", *Journal of Antibiotics*, 44 (1991), pp. 564–568.

*Primary Examiner*—Herbert J. Lilling
*Attorney, Agent, or Firm*—Sandra M. Nolan

[57] ABSTRACT

A certain fermentation product of Actinomadura strain Q473-8 yields, when suitably treated, a novel compound having both antibiotic and antitumor activities.

1 Claim, 4 Drawing Sheets

ANTITUMOR PROCESS EMPLOYING NOVEL FERMENTATE OF AN ACTINOMADURA STRAIN

This application is a divisional application of U.S. Ser. No. 07/780,516, filed Oct. 22, 1991.

RELATED APPLICATION

This application describes subject matter which is related to that disclosed in U.S. Ser. No. 464,046 filed Jan. 12, 1990, now U.S. Pat. No. 5,087,567.

BACKGROUND

It is known that antibiotic agents can be produced via the fermentation of a variety of types of microorganisms. Some biologically active chromophores are produced in such a way that they associate with protein moieties to form a chromoprotien complex. The chromoprotiens which have been studied are described in: "Neocarzinostatin chromophore", Napier, M. A., et. al. *Biochem. Biophys. Res. Commun.* 89, 635–642 (1979) and "Auromomycin Chromophore, Suzuki, H., et. al., *Biochem. Biophys. Res. Commun.* 94, 255–261 (1980). The antitumor antibiotic C-1027 is a chromophore fraction derived from *streptomyces globisporus* C-1027. Its isolation, characterization and biological activity are described by T. Otani et. al. in "Isolation and Characterization of Non-protein Chromophore and its Degradation Product from Antibiotic C-1027", *Journal of Antibiotics,* 44, 564–568 (1991).

THE INVENTION

The invention deals with a new compound BMY-46164, derived via the fermentation of a strain of *Actinomadura*, compositions and methods which use it and procedures for isolating it. It should be noted that applicants' references to "the compound" are intended to include all pharmaceutically acceptable derivatives of same.

The new fermentation product is believed, based upon high resolution fast atom bombardment mass spectrometry (FABMS) data, to have the molecular formula $C_{40}H_{43}N_2O_{12}Cl$ and a molecular weight of 778. It is a colorless, amorphous solid having the properties set out below.

This fermentation product is a non-protein, non-covalently bound chromophore which is associated, via what is believed to be complexing, with a protein produced from strains of Actinomadura.

The fermentation product has been found to exhibit antimicrobial activity against a variety of Gram positive organisms, i.e., *Enterococcus faecalis, Staphylococcus aureus,* and *Bacillus subtilis.* It also has activity in treating anti-tumor models, such as P388 leukemia.

The new antibiotic may be obtained by fermentation of a BMY-46164 producing strain or a mutant thereof, in an aqueous nutrient medium under submerged aerobic conditions until a substantial amount of BMY-46164 is produced by said microorganism in said culture medium. Fermentation is followed by recovery of BMY-46164 from the culture medium substantially free of co-produced substances.

MICROORGANISM DEPOSIT

A biologically pure culture of Actinomadura strain Q473-8, from which the compound of the invention is derived, has been deposited with the American Type Culture Collection (AATCC) in Rockville, MD and added to its permanent collection under Accession Code ATCC 53806.

Cultures of this strain are also maintained as lyophiles in the Bristol-Myers Squibb Company Pharmaceutical Research Institute Actinomycetes Culture Collection in Wallingford, Conn.

The ATCC deposit was made before the filing of this application and meets all of the requirements of 35 U.S.C. 112 regarding such deposits.

DRAWINGS

DESCRIPTION OF THE INVENTION

Figure 1:
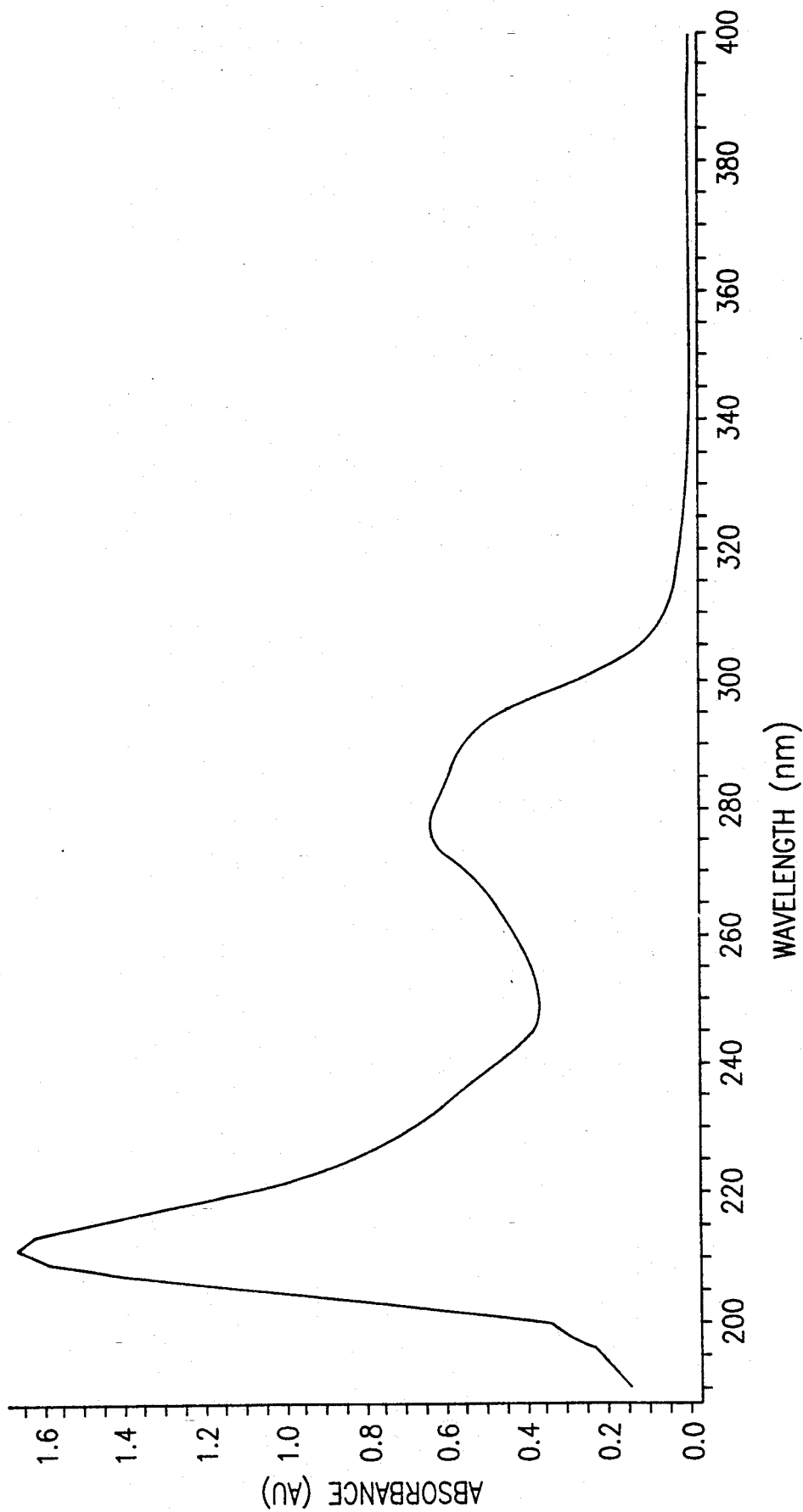
FIG. 1 shows the UV spectrum of BMY 46164 in methanol.
Figure 2:
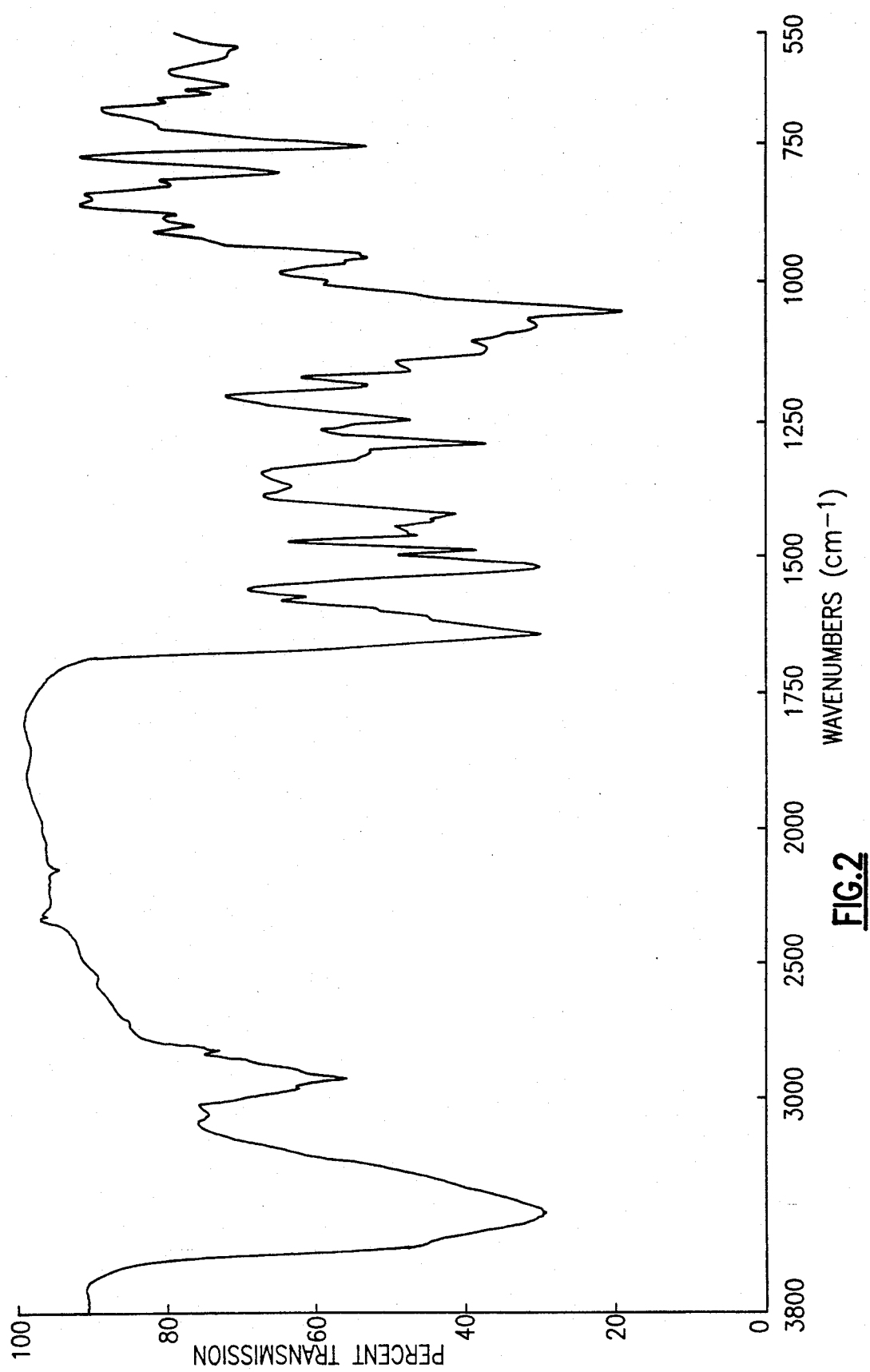
FIG. 2 shows the IR spectrum of BMY 46164 (KBr pellet).
Figure 3:
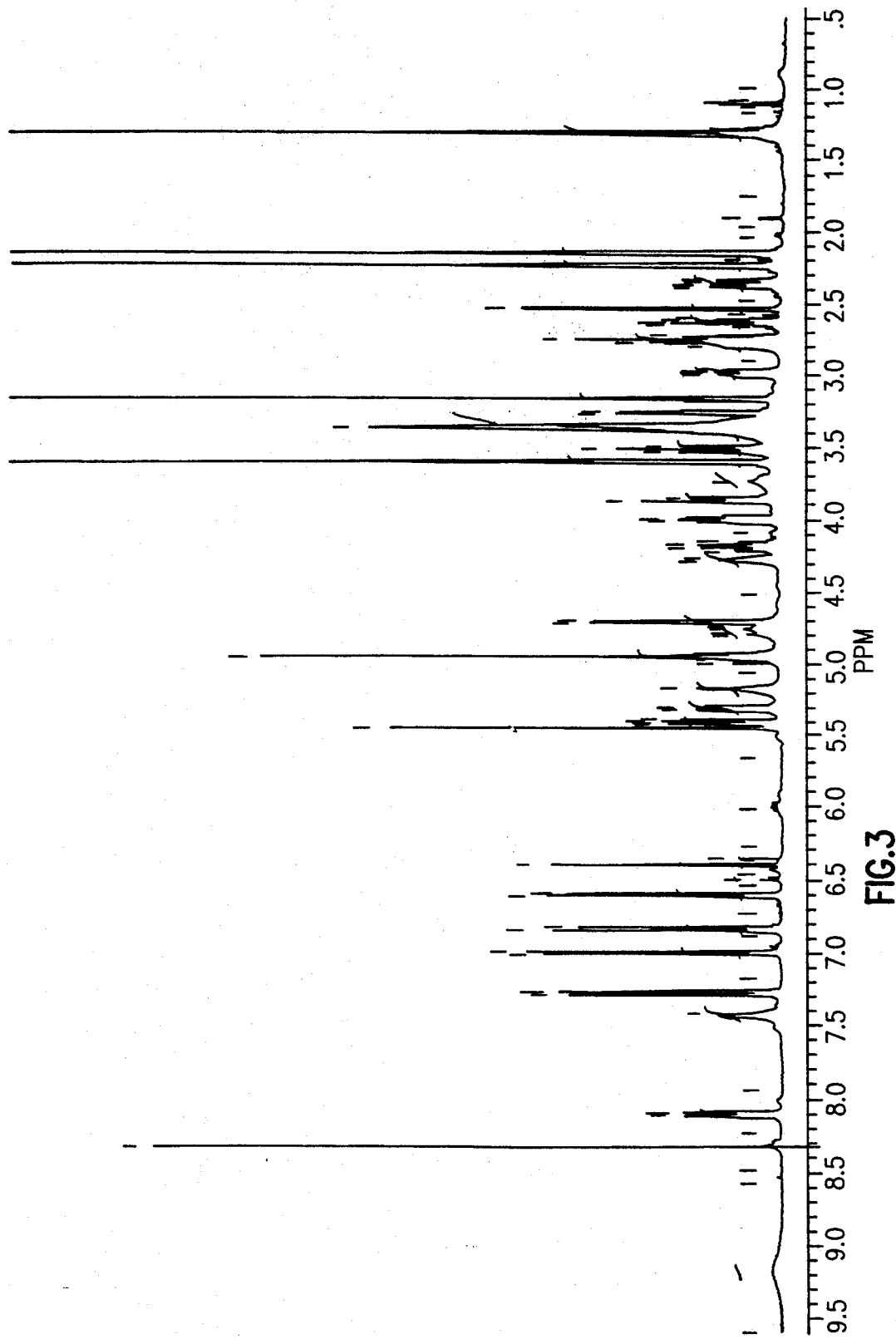
FIG. 3 shows the proton NMR spectrum of BMY 46164 in $d_6$-DMSO.
Figure 4:
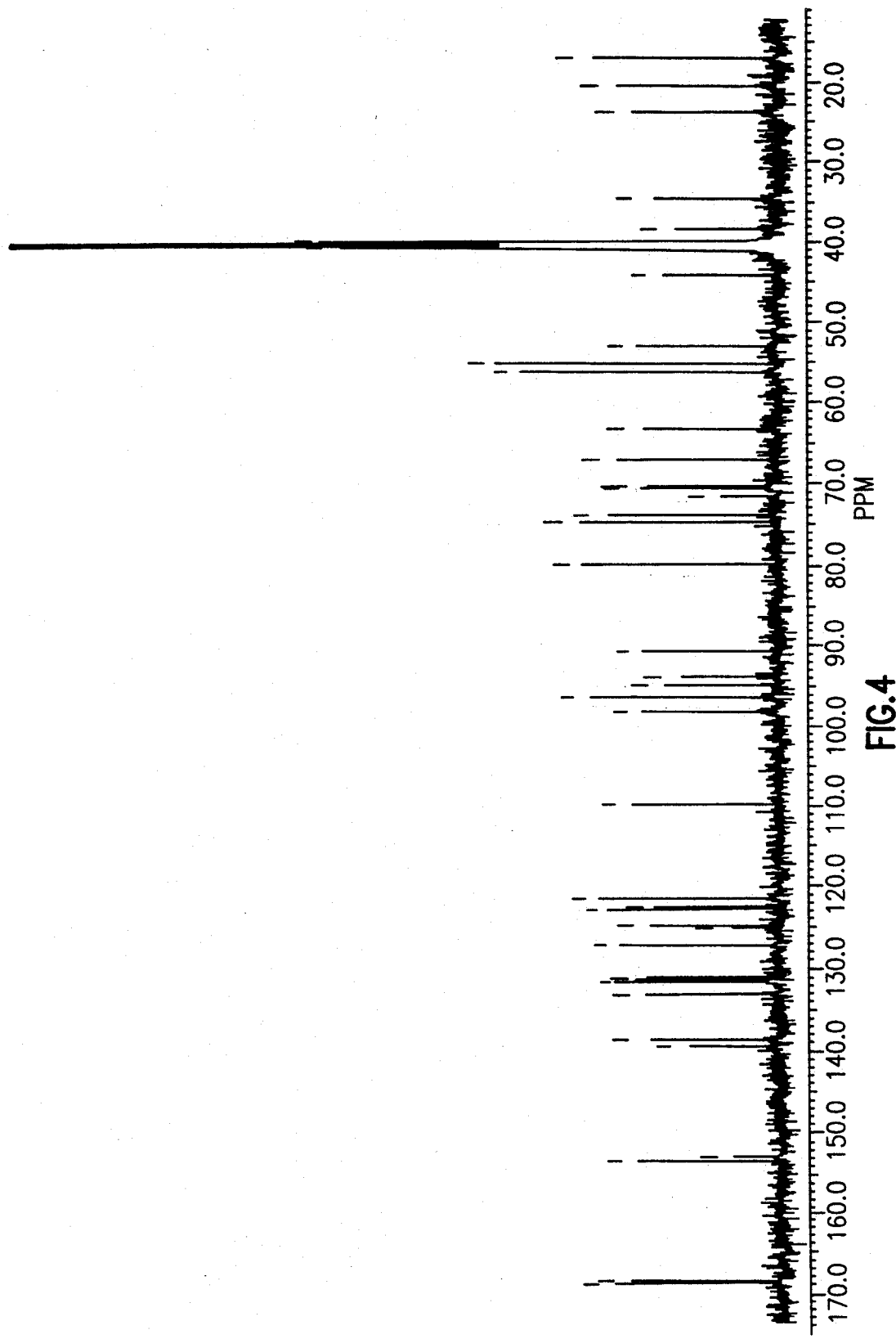
FIG. 4 shows the carbon NMR spectrum of BMY 46164 in $d_6$-DMSO.

The fermentation product, known as compound BMY-46164, has the empirical formula $C_{40}H_{43}N_2O_{12}Cl$ and a molecular Weight of 778.

One preferred process for producing BMY-46164 includes the steps of:

(1) fermenting a suitable strain of actinomycete, (2) extracting the proteinaceous fermentation product, (3) denaturing the product of step (2), and (4) isolating a compound having an emperical formula of $C_{40}H_{43}N_2O_2Cl$ and a molecular weight of 778.

A colorless amorphous solid, its chemical structure has not, as yet, been ascertained. However, its properties are:

Mass Spectrum: Kratos MS 50 TC Mass Spectrometer. FABMS: 778.2527. Also prominent fragment ions at 294.1339 and 149.0603.

Ultraviolet Spectrum: Hewlett Packard 8452A Diode Array Spectrometer; concentration 1.0 mg/100 ml methanol. A neutral solution gave the following absorption maximum $\lambda_{max}^{nm}(E^{1\%}_{1cm})$:278(635).

Infrared Spectrum: Perkin-Elmer 1800 FTIR spectrometer, KBr pellet, cm$^{-1}$: 1:3424, 3076, 2934, 2838, 2170, 1640, 1578, 1520, 1490, 1462, 1424, 1376, 1292, 1248, 1184, 1156, 1112, 1072, 1046, 952, 900, 880, 832, 810, 754, 682, 666, 648, 576, 524.

500 MHz $^1$H-NMR: Bruker Model AM-500 Spectrometer. Dual carbon-proton probe, 5mm. Solvent $d_6$-DMSO. Observed chemical shifts (ppm): 9.18 (br. 5, 1H), 8.09 (dd, 1H), 7.40 (d, 1H), 7.25 (d, 1H), 6.97 (d, 1H), 6.81 (d, 1H), 6.58 (d, 1H), 6.37 (t, 1H), 5.41 (s, 1H), 5.37 (dd, 1H), 5.27 (m, 1H), 5.13 (br. s, 1H), 4.91 (s, 1H), 4.89 (m, 1H), 4.65 (d, 1H), 4.22 (br. d, 1H), 4.13 (ddd, 1H), 3.94 (m, 1H), 3.80 (dd, 1H), 3.54 (s, 3H), 3.46 (dd, 1H), 3.21 (d, 1H), 3.12 (s, 3H), 2.94 (ddd, 1H), 2.73 (m, 1H), 2.71 (dd, 1H), 2.58 (dd, 1H), 2.31 (dd, 1H), 2.19 (s, 3H), 2.10 (s, 3H), 1.26 (s, 3H).

125 MHz $^{13}$C NMR: Bruker Model AM-500 Spectrometer. Proton decoupled spectrum. Dual carbon-proton probe, 5mm. Solvent $d_6$-DMSO. Observed chemical shifts (ppm): 168.4, 168.1, 153.3, 152.8, 139.3, 138.5, 133.0, 131.4, 131.3, 131.0, 130.8, 126.8, 124.7, 124.3, 122.5, 122.1, 121.0, 109.2, 97.5, 95.7, 94.3, 94.2, 93.3, 90.1, 74.0, 73.2, 70.9, 69.8, 69.6, 66.3, 62.5, 55.4, 54.4, 52.3, 43.2, 37.5, 33.6, 22.7, 19.5, 16.1.

In all of the procedures described herein, the following parameters were employed:

Solvents were not redistilled before use. Methanol, ethyl acetate, chloroform, hexanes, diethyl ether, methylene chloride and acetonitrile were ACS reagent grade. Water for HPLC refers to in-house deionized water from a Barnstead Nanopure II system. Methanol and acetonitrile for HPLC use were B&J Brand HPLC grade solvents. Ammonium acetate was Fisher HPLC grade. DEAE cellulose was Schleicher and Schuell Anion exchange cellulose (lots 2932 and 2893). Tris buffer [tris (hydroxymethyl) aminomethane] was enzyme grade ultra pure (Bethesda Research Laboratories), 0.05 M, pH 7.4. Dicalite was speed plus grade filter aid (Grefco Minerals).

Normal phase thin layer chromatograph (TLC) was carried out on silica gel 60, $F_{254}$ plates (EM Reagents, cat. #5765, 5×10 cm, by 0.25 mm thick). Reversed phase TLC was accomplished with Whatman $MKC_{18}$ developed (cat. #4803-110, 0.2 mm thick). Plates were developed in Whatman cylindrical jars with caps and 10 ml of eluant. Chromophores were visualized as UV quenching zones with 254 nm ultraviolet light.

Preparative layer chromatography (PLC) was carried out on silica gel 60, $F_{254}$ plates (EM Reagents, cat. #5766, 20×20 cm, by 2 mm thick). Plates were developed in glass tanks with covers and 100 mL of eluant.

The vacuum liquid chromatography (VLC) apparatus consisted of Buchner funnel (Kontes, Art. #K-954100) containing a sealed-in sintered glass disc (M porosity), a side hose connection for vacuum and a lower 24/40 joint for attachment of receiving flasks. The funnels were equilibrated by pulling the initial eluant through under vacuum to form tightly packed 5 cm adsorbent bed heights. Samples were preadsorbed onto adsorbent and applied to funnels as slurries in the starting eluant. Step gradients were carried out using predetermined volumes of increasingly more polar eluant. The funnel was sucked dry after each volume. Fractions were concentrated on a rotary evaporator and combined on the basis of in vitro bioassay results in conjunction with HPLC-UV and TLC analyses.

Dicalite chromatography refers to adsorption chromatography on diatomaceous earth. Samples were dissolved in chloroform—methanol (2:1) and adsorbed onto dicalite. The resulting powders were slurried in hexanes and packed into sintered glass VLC funnels. Predetermined volumes of solvents were pulled through the dicalite into round bottomed flasks which were concentrated on a rotary evaporator.

Apparatus for size exclusion chromatography consisted of the following: A Glenco column (2.5 I.D. ×100 cm) equipped with solvent resistant Teflon end plates; Fluid Metering, Inc. FMI lab pump (Model RP-G1 50); Glenco glass reservoir (500 ml); Isco Model 328 fraction collector. Columns were slurry packed with 150 g of Sephadex LH-20 (Pharmacia) preswollen in the eluting solvent. Solvent was delivered in a downward manner through the column at a rate controlled by the lab pump.

HPLC purifications were carried out on a Beckman System Gold unit consisting of the following components: Model 126 solvent delivery module; Model 166P programmable detector; solvent reservoir kit; Altex injector; Dynamax 60°A semi-prep columns; normal phase silica gel (25 cm×10 mm, 8 microns, Si-83-1111-C) or (25 cm×21.4 mm, 8 microns, Si-83-121-C) and reversed phase (25 cm×10 mm, 8 microns, $C_{18}$-83-211-C).

The antibiotic antitumor agent of the invention may be produced by fermentation of a BMY-46164 producing strain of actinomycete. The preferred producing organism is an actinomycete isolated from a soil sample collected in Athens, Greece, and designated strain Q473-8. A biologically pure culture of strain Q473-8 has been deposited with ATCC as described above.

Taxonomic studies on strain Q473-8 have been described in detail in U.S. Pat. application Ser. No. 464,046. The chemotaxonomic data, together with the morphological features of strain Q473-8, indicate that the organism is a member of the genus Actinomadura, most closely resembling *Actinomadura madurae* in its morphology and carbon utilization characteristics. See Williams et al., "The Prokaryotes, Vol II", pp. 2103-17, 1981 (Starr, Stolp, Truper, Balows and Schlegel, eds.)

Further characterization, including menaquinone analysis, is needed to determine whether strain Q473-8 has properties consistent with a recently proposed new genus, *Nonomuria*. See Goodfellow et. al., "Biology of Actinomycetes, 1988" pp. 223-38, 1988 (Okami, Beppu and Ogawara, eds.)

It is to be understood that the present invention is not limited to the use of the particular preferred strain described above or to organisms fully answering its description. It is especially intended to include other BMY-46164 producing variants or mutants of the described organism which can be produced by conventional means such as x-ray radiation, ultraviolet radiation, treatment with nitrogen mustards, phage exposure and the like.

BMY-46164 may be produced by cultivating a BMY-46164 producing strain of an Actinomadura species, preferably strain Q473-8 or a mutant or variant thereof, under submerged aerobic conditions in an aqueous nutrient medium.

The organism is grown in a nutrient medium containing an assimilable carbon source, for example, sucrose, lactose, glucose, rhamnose, fructose, mannose, melibiose, glycerol or soluble starch. The nutrient medium should also contain an assimilable nitrogen source, such as peptone, fish meal, soybean flour, peanut meal, cottonseed meal, corn steep liquor, yeast extract or ammonium salts. Inorganic salts, such as sodium chloride, potassium chloride, magnesium sulfate, calcium carbonate, phosphates, etc., may be added if desired.

Trace elements, such as copper, manganese, iron, zinc, etc., are added to the medium if desired, or they may be supplied as impurities of other constituents of the media.

Production of BMY-46164 can be effected at any temperature conducive to the satisfactory growth of the producing organism, e.g., at about 16° to about 41° C. It is preferable to conduct the fermentation at about 25° to about 35° C., most preferably at about 27° to about 32° C. A neutral pH is preferably employed in the medium. Production of the antibiotic is carried out generally for a period of about four to about five days.

The fermentation may be carried out in flasks or in laboratory or industrial fermentors of various capacities. When tank fermentation is to be used, it is desirable to produce a vegetative inoculum in a nutrient broth by inoculation of a small volume of the culture medium with a slant or a lyophilized culture of the organism.

After obtaining an active inoculum in this manner, it is transferred aseptically to the fermentation tank medium for large scale production of BMY-46164. The medium in which the vegetative inoculum is produced can be the same as, or different from, that utilized in the tank, so long as it is such that a good growth of the producing organism is obtained. Agitation during the fermentation can be provided by a mechanical impeller. Conventional antifoam agents, such as lard oil or silicon oil, can be added if desired.

Isolation of BMY-46164 antibiotic from the fermentation medium and purification of BMY-46164 can not be achieved by conventional solvent extraction and chromatographic techniques. Instead, isolation is achieved via the following procedure.

Whole broth (90 liters) was filtered with the aid of Dicalite. To the filtrate was added 1 kg of DEAE cellulose with thorough mixing and cooling to 4° C. The DEAE cellulose was recovered by filtration and rinsed with fresh chilled (4° C.) tris buffer. The DEAE cellulose mat was extracted by standing for one hour in a 6 liter mixture of methanol-ethyl acetate (1:1). The extraction mixture was filtered, and the resulting cellulose mat rinsed with additional ethyl acetate (3 liters). To the combined organic extract was added 6 liters chilled $H_2O$. The ethyl acetate layer was separated and concentrated under reduced pressure to yield 1.0 g crude chromophore extract.

An alternate way to obtain chromophore extract was to substitute methylene chloride for ethyl acetate in the partitioning step. Thus, to one volume of methanol, obtained from extracting the protein-bound DEAE cellulose mat, was added two volumes of chilled water (20 C.) and one volume of methylene chloride. The organic layer was concentrated on a rotary evaporator to yield crude chromophore extract.

The chromophore extract (1.0 g) was adsorbed onto 3.5 g of Universal silica gel (63-200 microns) and applied to a 60 ml VLC funnel containing 25 g Lichroprep Si 60 silica gel (EM Science, Art. 9390, 25-40 microns). A chloroform-methanol step gradient was carried out using 300 ml volumes of eluant. The activity eluted in fractions 3-5 as determined by in vitro assays. The composition of eluant in these fractions was chloroform containing 3% MeOH, 5% MeOH and 8% MeOH respectively. These combined fractions (202 mg) were further purified by preparative layer chromatography (PLC) using CHCl$_3$-MeOH (90:10) for development.

The recovered main band of activity ($R_f$ 0.37, 48 mg) was subjected to further purification by HPLC on a Dynamax semi-prep silica gel column (Si-83-111-C) using isocratic conditions (CHCl$_3$-MeOH 94:6) at 4 ml/minute. The main peak eluted at 13.3 minutes as indicated by UV detection (254 nm). The peak was collected and evaporated to dryness. The residue (28 mg) was applied to a second Merck PLC plate. Development was made with chloroform-acetonitrile (60:40). The main recovered band ($R_f$ 0.15) has a mass of 16.5 mg.

Final purification was effected with reversed phase HPLC using a Dynamax semi-prep column (C$_{18}$-83-211-C). A gradient elution was carried out 20% A—80% B→40% A—60% B over 40 minutes, where A=acetonitrile, B=0.1 M ammonium acetate-methanol (3:1). The desired chromophore (11 mg) eluted at 30.9 minutes and was designated as BMY-46164.

Another purification process to obtain BMY-46164 from crude chromophore extract was carried out as follows: Crude extract (12.9 g) was dissolved in chloroform-methanol 2:1 and adsorbed onto 300 g of dicalite (diatomaceous earth). The Dicalite bed was washed with 1 liter volumes of the following solvents: hexanes; diethyl ether; ethyl acetate; methylene chloride and methanol. BMY-46164 was concentrated in the diethyl ether and ethyl acetate fractions, which had a combined mass of 0.6 g.

This residue was dissolved in 5 ml of chloroform-methanol (1:1) and applied to a Sephadex LH-20 column preswollen with the same solvent. The flow rate was 1.5 ml/min. Five fractions were collected. BMY-46164 eluted mainly in the third fraction at 0.7 bed volumes. Upon concentration, this fraction weighed 143 mg.

Final purification was accomplished by normal phase HPLC using a 21.4 mm Dynamax preparative column (Si-83-121-C) at 10 ml/min. A gradient elution was carried out from chloroform-methanol (95:5) to chloroform-methanol (85:15) over 40 minutes. Detection was at 300 nm. BMY-46164 (34 mg) eluted at 27.7 minutes.

Compositions employing as drugs the compound BMY-46164 and/or its acid or base addition salts may contain suitable amounts of other ingredients. Generally, from about 0.001 to 99.99% of one or more pharmaceutically acceptable excipients, such as fillers, carriers, stabilizers, gellants, colorants, perfumes and the like can be used. The content of the drug(s) in such compositions will generally be from about 0.01% to about 10% preferably about 0.17% to about 5%.

EXAMPLES

The following preferred specific embodiments are intended to be merely illustrative and not to limit the scope of the invention.

EXAMPLE 1

Fermentation of BMY-46164 in Shake Flasks

Strain Q473-8 was maintained and transferred in test tubes on agar slants of yeast extract-malt extract supplemented with CaCO$_3$. This medium consists of 4.0 gm of dextrose, 4.0 gm yeast extract, 10 gm of malt extract, 1.5 gm calcium carbonate and 15 gm of agar, made up to one liter with distilled water. With each transfer, the agar slant was incubated for 5 to 7 days at 28° C.

To prepare an inoculum for the production phase, the surface growth from the slant culture was transferred to a 500 ml Erlenmeyer flask containing 100 ml of a vegetative medium consisting of 2% glucose, 1% fishmeal and 0.5% calcium carbonate. The vegetative medium was incubated for 3 days at 28° C. on a rotary shaker set at 250 rev/min.

Five ml of this vegetative growth were transferred to a 500 ml Erlenmeyer flask containing 100 ml of the production medium consisting of 2% glucose, 2% peptone and 0.5% calcium carbonate. The production medium was again incubated for 4 to 5 days at 28° C. on a rotary shaker set at 250 rev/min. The culture produced maximum levels of BMY-46164 about 4 days into the fermentation cycle.

EXAMPLE 2

Fermentation of BMY-46164 in Laboratory Fermentors

For fermentation in a 50 liter nominal volume Biolafitte fermentor, a two stage vegetative medium was used. Sixteen ml of a vegetative culture as per Example 1 were transferred to a two liter Erlenmeyer flask containing 400 ml of a second vegetative medium consisting of 2% glucose, 2% peptone and 0.5% calcium carbonate. This second vegetative culture was incubated for three days at 28° C. on a rotary shaker set at 250 rev/min.

1,200 ml of this vegetative culture were transferred to a 4 liter Vitro bottle and then inoculated into a 50 liter nominal volume Biolafitte fermentor containing 30 liters of the production medium consisting of 2% glucose, 2% peptone and 0.5% calcium carbonate. The organism was allowed to grow under the following conditions: agitation, 250 rpm; temperature, 28° C.; aeration, 30 liters/min. An antifoam agent (polypropylene glycol 2,000, Dow Chemical) was used to control foaming. BMY-46164 reached maximum production levels within four to five days of the start of the fermentation cycle.

EXAMPLE 3
Bacterial Activity Study

Using the procedure described below, the performance of BMY-46164 was compared to that of ampicillin for its affect on a series of microorganisms. Table 1 shows the results.

TABLE 1
Performance of BMY-46164 as an Antibacterial Agent

| ORGANISM | PRIMARY MIC VALUES (μg/ml) | |
|---|---|---|
| | BMY-46164 | AMPICILLIN |
| Enterococcus faecalis A20688 | 8 | .25 |
| E. faecalis A25707 | 4 | 25 |
| E. faecalis A25708 | 8 | .5 |
| Staphylococcus aureus A9537 | 4 | .06 |
| S. aureus/NCCLS strain | 16 | .06 |
| S. aureus | 16 | .5 |
| Escherichia coli A15119 | >500 | 1 |
| E. coli/NCCLS strain | >500 | 2 |
| E. coli A9751 | >500 | .25 |
| Klebsiella pneumoniae A20468 | >500 | 16 |
| K. pneumoniae A20468 | >500 | 32 |
| Proteus vulgaris A21559 | >500 | 32 |
| Pseudomonas aeruginosa A9843 | >500 | >128 |
| P. aeruginosa A20235 | >500 | 32 |
| P. aeruginosa/NCCLS strain | >500 | >128 |
| Bacillus subtilis A9506-A | 64 | 1 |

The antibacterial spectrum of BMY-46164 was determined by serial broth dilution method using nutrient broth (Difco).

EXAMPLE 4
Antitumor Activity Study

The performance of BMY-46164 as an antitumor agent against P388 leukemia was tested in mice. Table 2 shows the results for olivomycin A and BMY-46164.

TABLE 2
Performance of BMY-46164 as an Antitumor Agent
TUMOR: P388

| MATERIAL(S) AND VEHICLE | TREATMENT MG/KG/DOSE RTE, SCHEDULE OR DILUTION | MED. S.T. | % T/C | AWC, GM D.6 | NO. MICE ALIVE/TOT D.5 (30) |
|---|---|---|---|---|---|
| IMPLANT LEVEL AND SITE: | 1 × 10(6) CELLS, IP | | | | |
| OLIVOMYCIN A | 0.8 IP, Q01DX5;1 | 15.0 | 150 | −0.2 | 6/6 |
| BMY33272 | 0.4 | 14.5 | 145 | 0.9 | 6/6 |
| PBS | | | | | |
| C39174 W0002 G443 | 25 IP, Q01DX5;1 | 12.5 | 125 | −2.1 | 4/4 |
| BMY46164 | 10 | 14.0 | 140 | −0.9 | 4/4 |
| DMSO+PBS | 5 | 15.5 | 155 | 0.3 | 4/4 |
| | 2 | 14.0 | 140 | 0.2 | 4/4 |
| CONTROL | | 10.0 | 100 | 2.5 | 10/10 |

The procedure used in obtaining the data in Table 2 was described in "Transplanted Animal Tumors", Bradner, W. T., *Cancer and Chemotherapy* Vol. 1, pp. 221-227, 1980 (S. T. Crooke and A. W. Prestayko, eds.), Academic Press.

These examples illustrate the utility of the subject compound and its pharmaceutically acceptable derivatives in the treatment of bacterial infections and neoplastic tumors in hosts.

By "hosts" is meant not only in vitro test cells and mice, but also higher organisms, e.g. mammals. Human subjects or patients are a preferred group of hosts to be treated.

The compounds and compositions of the invention can be administered to suitable hosts, e.g., to patients suffering from bacterial infections and/or tumors, via a variety of means. Oral, parenteral, topical, nasal, buccal and ocular formulations are contemplated.

Reasonable variations, such as those which would occur to a skilled artisan, can be made herein without departing from the scope of the invention.

We claim:

1. A process for treating a tumor in a patient suffering therefrom comprising the step of administering to said patient an antitumor effective amount of the compound BMY-46164 isolated from a fermentation product of Actinomadura strain Q473-8, which compound has an empirical formula of $C_{40}H_{43}N_2O_{12}Cl$, a molecular weight of 778, and the following spectral properties:

(a) Mass Spectrum: FABMS: 778.2527, with prominent fragment ions at 294.1339 and 149.0603;

(b) Ultraviolet Spectrum: A neutral 1.0 mg/100 ml methanol solution had absorption maximum $\lambda_{max\text{-}nm}(E^{1\%}_{1cm})$: 278 (635);

(c) Infrared Spectrum: KBr pellet, $cm^{-1}$: 3424, 3076, 2934, 2838, 2170, 1640, 1578, 1520, 1490, 1462, 1424, 1376, 1292, 1248, 1184, 1156, 1112, 1072, 1046, 952, 900, 880, 832, 810, 754, 682, 666, 648, 576, 524;

(d) 125 MHz $^{13}C$ NMR: Bruker Model AM-500 Spectrometer, Proton decoupled spectrum. Dual carbon-proton probe, 5 mm. Solvent $d_6$-DMSO. Observed chemical shifts (ppm): 168.4, 168.1, 153.3, 152.8, 139.3, 138.5, 133.0, 131.4, 131.3, 131.0, 130.8, 126.8, 124.7, 124.3, 122.5, 122.1, 121.0, 109.2, 97.5, 95.7, 94.3, 94.2, 93.3, 90.1, 74.0, 73.2, 70.9, 69.8, 69.6, 66.3, 62.5, 55.4, 54.4, 52.3, 43.2, 37.5, 33.6, 22.7, 19.5, 16.1;

(e) 500 MHz $^1H$-NMR: Bruker Model AM-500 Spectrometer. Dual carbon-proton probe, 5 mm. solvent $d_6$-DMSO. Observed chemical shifts (ppm): 9.18 (br. 5, 1H), 8.09 (dd, 1H), 7.40 (d, 1H), 7.25 (d,1H), 6.97 (d, 1H), 6.81 (d, 1H), 6.58 (d, 1H), 6.37 (t, 1H), 5.41 (s, 1H), 5.37 (dd, 1H), 5.27 (m, 1H), 5.13 (br. s, 1H), 4.91 (s, 1H), 4.89 (m, 1H), (d, 1H), 4.22 (br. d, 1H), 4.13 (ddd, 1H), 3.94 (m, 1H), 3.80 (dd, 1H), 3.54 (s, 3H), 3.46 (dd, 1H), 3.21 (dd, 1H), 3.12 (s, 3H), 2.94 (ddd, 1H), 2.73 (m, 1H), 2.71 (dd, 1H), 2.58 (dd, 1H), 2.31 (dd, 1H), 2.19 (s, 3H), 2.10 (s, 3H), 1.26 (s, 3H) or pharmaceutically acceptable acid or base addition products thereof.

* * * * *